United States Patent
Podrebarac

(10) Patent No.: US 11,920,078 B2
(45) Date of Patent: Mar. 5, 2024

(54) HEAT STORAGE IN CHEMICAL REACTORS

(71) Applicant: LUMMUS TECHNOLOGY LLC, Bloomfield, NJ (US)

(72) Inventor: Gary George Podrebarac, Friendswood, TX (US)

(73) Assignee: LUMMUS TECHNOLOGY LLC, Houston, TX (US)

( * ) Notice: Subject to any disclaimer, the term of this patent is extended or adjusted under 35 U.S.C. 154(b) by 45 days.

(21) Appl. No.: 17/100,708

(22) Filed: Nov. 20, 2020

(65) Prior Publication Data

US 2021/0147737 A1 May 20, 2021

Related U.S. Application Data

(60) Provisional application No. 62/937,983, filed on Nov. 20, 2019.

(51) Int. Cl.
| | | |
|---|---|---|
| C07C 5/333 | (2006.01) | |
| C01F 11/24 | (2006.01) | |
| C09K 5/00 | (2006.01) | |
| C09K 5/06 | (2006.01) | |
| C07C 9/08 | (2006.01) | |
| C07C 9/12 | (2006.01) | |

(52) U.S. Cl.
CPC ............. *C09K 5/063* (2013.01); *C01F 11/24* (2013.01); *C07C 5/333* (2013.01); *C07C 9/08* (2013.01); *C07C 9/12* (2013.01)

(58) Field of Classification Search
CPC ......... C09K 5/063; C01F 11/24; C07C 5/333; C07C 5/3332; C07C 5/3335; C07C 5/3337; C07C 5/42; C07C 5/44; C07C 5/46; C07C 5/48; C07C 5/50; C07C 5/52; C07C 5/54; C07C 5/56; C07C 9/08; C07C 9/12; B01J 2208/00017; B01J 2208/00805; B01J 2208/00814; B01J 2208/025; B01J 2208/065; B01J 8/02; B01J 8/06; B01J 8/067; B01J 8/08; B01J 8/082; B01J 8/087; B01J 8/18; B01J 8/1809; B01J 8/1836
See application file for complete search history.

(56) References Cited

U.S. PATENT DOCUMENTS

| | | | |
|---|---|---|---|
| 6,191,332 B1 | 2/2001 | Duee et al. | |
| 7,569,738 B2 | 8/2009 | Ledoux et al. | |
| 9,950,971 B2 * | 4/2018 | Henao | B01J 29/7088 |
| 2004/0199034 A1 | 10/2004 | Walsdorff et al. | |
| 2010/0030004 A1 | 2/2010 | Han et al. | |
| 2015/0065769 A1 | 3/2015 | Henao et al. | |
| 2015/0190796 A1 * | 7/2015 | Bedel | C07C 1/0435 241/3 |
| 2016/0168052 A1 * | 6/2016 | Schwint | B01J 8/02 422/187 |
| 2017/0283258 A1 | 10/2017 | Hornung et al. | |

FOREIGN PATENT DOCUMENTS

| | | |
|---|---|---|
| CN | 108176405 A | 6/2018 |
| JP | 2016155120 A | 9/2016 |

OTHER PUBLICATIONS

Pattison, R. C. et al, "Robust autothermal microchannel reactors", Computers & Chemical Engineering, 2015, vol. 81, pp. 171-179 (9 pages).
International Search Report issued in International Application No. PCT/US2020/061646 dated Mar. 18, 2021 (5 bages).
Written Opinion issued in International Application No. PCT/US2020/061646 dated Mar. 18, 2021 (6 pages).
Examination Report issued in corresponding GC Application No. 40939 dated Sep. 30, 2021 (4 pages).
Extended European Search Report issued in European Application No. 20889762.9 dated Nov. 28, 2023 (10 pages).
Zawaz, "Light alkane dehydrogenation to light olefin technologies: a comprehensice review", Rev Chem Eng 2015: 31(5): 413-436 (24 pages).

* cited by examiner

*Primary Examiner* — In Suk C Bullock
*Assistant Examiner* — Jason Y Chong
(74) *Attorney, Agent, or Firm* — Osha Bergman Watanabe & Burton LLP

(57) ABSTRACT

A process for producing olefins may include dehydrogenating a first alkane in a first reactor to produce a first effluent comprising at least one of a first n-olefin or a first diolefin; removing the first effluent from the first reactor; and regenerating the first reactor. The first reactor may include a first dehydrogenation catalyst and a first phase change material.

17 Claims, No Drawings

HEAT STORAGE IN CHEMICAL REACTORS

BACKGROUND

Many industrially-important catalytic reactions are endothermic and effect a decrease in reactor temperature. To counteract this temperature drop, which may negatively influence several reaction parameters, heat needs to be added to the reactor to sustain the reaction.

One such endothermic process is the dehydrogenation of aliphatic hydrocarbons, which generates olefins useful for the production of a number of petrochemical products. Short chain saturated hydrocarbons having from 2 to 5 carbon atoms per molecule are often subjected to dehydrogenation to form the corresponding olefin. The olefins, in turn, may be used in the alkylation of isoparaffins, in the etherification of alcohols to make motor fuel blending additives, or as monomers used to produce various polymer materials. Olefins can also undergo subsequent dehydrogenation to diolefins.

A particularly useful olefin is propylene, which may be produced by dehydrogenation of propane. Propylene is the world's second largest petrochemical commodity and is used in the production of polypropylene, acrylonitrile, acrylic acid, acrolein, propylene oxide and glycols, plasticizer oxo-alcohols, cumene, isopropyl alcohol and acetone. The growth in propylene production is primarily driven by the industry demand for polypropylene, which is used in such everyday products as packaging materials and outdoor clothing. Other useful olefins include butene, isobutene, and isopentene, which have equally diverse end uses.

A particularly useful diolefin is butadiene, which may be produced by dehydrogenation of n-butene. Butadiene is used primarily as a chemical intermediate and as a monomer in the manufacture of polymers such as synthetic rubbers or elastomers, including styrene-butadiene rubber (SBR), polybutadiene rubber (PB R), polychloroprene (Neoprene) and nitrile rubber (NR). Another useful diolefin is isoprene. The major applications of isoprene include use as a monomer for the manufacture of polyisoprene rubber, styrene-isoprene-styrene block copolymers (SIS) and butyl rubber.

The dehydrogenation of aliphatic hydrocarbons may be performed by a cyclic, adiabatic process such as the CATOFIN® process. Each cycle of the CATOFIN® process requires reduction of the catalyst, dehydrogenation of the hydrocarbon, purging, and regeneration. The endothermic dehydrogenation reaction decreases the temperature of the catalyst bed which, coupled with coke deposits, decreases its ability to produce the desired products. Conventionally, the regeneration step provides hot air to the reactor to remove the coke and to restore the necessary heat to the catalyst bed. However, this regeneration is often not able to evenly heat the reactor and cannot provide full utilization of the catalyst.

SUMMARY OF INVENTION

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to processes for producing olefins may include dehydrogenating a first alkane in a first reactor to produce a first effluent comprising at least one of a first n-olefin or a first diolefin; removing the first effluent from the first reactor; and regenerating the first reactor. The first reactor may include a first dehydrogenation catalyst and a first phase change material.

In a further aspect, embodiments disclosed herein relate to reactors that include a dehydrogenation catalyst, and a phase change material. The phase change material may undergo a phase transition at a temperature of 525° C. or more and 675° C. or less.

Other aspects and advantages will be apparent from the following description and the appended claims.

DETAILED DESCRIPTION

One or more embodiments disclosed herein generally relate to reactors that incorporate a phase change material (PCM). The PCM may advantageously provide heat to one or more regions of the reactor, such as to a catalyst. When used in an endothermic process of one or more embodiments, the heat provided by the PCM may, to some degree, counteract the decrease in temperature that arises from the heat-absorbing reaction, and enable the catalytic reaction to be prolonged. Other embodiments disclosed herein are directed to processes that may use a PCM-containing reaction to perform an endothermic reaction.

By carefully selecting a PCM with an appropriate phase transition temperature, a practitioner can take advantage of an exothermic phase-transition to provide heat to a reaction. Thus, the PCM may provide a much higher capacity to store and release heat when compared with typical components used in reactors. This may be useful for a wide variety of endothermic processes but is particularly advantageous for reactors that operate dynamically or batch-wise, or for situations where the catalyst is used to carry the needed heat of reaction. Examples may include cyclical processes that only have a catalyst in operation for fairly short period of time. Examples may include CATOFIN® reactors, reactors for catalytic cracking (such as fluid catalytic cracking, FCC), batch reactors, and cyclic catalytic reforming reactors.

In the CATOFIN® process, for example, the dehydrogenation reactor periodically stops operating due to lack of heat and needs to be regenerated/reheated. Having a PCM incorporated as part of the catalyst bed may allow the reactor to operate for a longer period of time before regeneration is needed.

Phase-Change Materials

A PCM in accordance with embodiments of the present disclosure may be a material that undergoes a phase change under conditions found in a reactor during a chemical reaction. The PCM is not particularly limited and may be any material consistent with this disclosure that stores thermal energy via the latent heat of phase transitions. The PCM may, for example, undergo any exothermic phase change, such as a solid-to-solid (SS), a liquid-to-solid (freezing), a gas-to-liquid (condensation), or a gas-to-solid (deposition) transition. With the benefit of this disclosure, one of ordinary skill in the art will appreciate that the nature of the phase change will influence the arrangement and containment of the PCM in a reactor. In some embodiments, one or more PCMs may be used in combination.

In one or more embodiments, PCMs exhibiting a solid-to-solid phase transition (SS-PCM) or a liquid-to-solid phase transition may be preferable. Such PCMs may not require encapsulation and provide a small change in volume upon undergoing the phase transition. Further, SS-PCMs limit the potential formation of leaks.

PCMs in accordance with the present disclosure will generally change phase at a high temperature and be thermally stable. The PCM may be selected to undergo its phase transition at a temperature that will be accessed by the reactor in which it is being used. For instance, a reactor may have an initial temperature of 690° C. and a PCM may have a phase-transition temperature of 610° C. As the endothermic reaction is performed, the reactor, and the PCM, will cool. Once the temperature of the PCM reaches 610° C., a phase-transition will occur, releasing heat and sustaining the chemical reaction.

In one or more embodiments, the PCM may have a phase transition temperature ranging from about 300° C. to about 700° C. For example, the PCM may have a phase transition temperature that ranges from a lower limit of any of 300, 350, 400, 450, 500, 550, or 600° C. to an upper limit of any of 400, 450, 500, 550, 600, 650, or 700° C., where any lower limit can be used in combination with any upper limit. In some embodiments, where the PCM is used in a CATOFIN® process, the PCM may specifically have a phase transition temperature ranging from about 550° C. to about 650° C. For example, the PCM may have a phase transition temperature that ranges from a lower limit of any of 550, 570, 590, 600, 610, 620, or 630° C. to an upper limit of any of 570, 590, 600, 610, 620, 630, or 650° C., where any lower limit can be used in combination with any upper limit.

The PCM of particular embodiments may be selected to be catalytically inert toward one or more, but preferably all, of the feedstock, the products, and any intermediates generated for a particular process. Using a PCM that is catalytically inert under the conditions of the reactor may favorably limit the production of side products and may enhance the selectivity and/or efficiency of the process. The PCM may be produced by any method that is known in the art.

The PCM of one or more embodiments may comprise one or more metal salts and/or metal alloys. PCMs in accordance with the present disclosure may include $NaNO_3$, $CaCl_2$/NaCl, Al, Si/Al, $BaCl_2$ or Zn. In particular embodiments, the PCM may comprise a mixture of 35.9 mol % $BaCl_2$ and 64.1 mol % $CaCl_2$, providing a melting point of about 608° C. One of ordinary skill will appreciate that the composition of a PCM may influence both the latent heat of its phase transition (i.e. its ability to store heat) as well as its phase transition temperature (i.e. its suitability for use in a given process).

The PCM of one or more embodiments may be enclosed, which may advantageously inhibit corrosion. The enclosure of one or more embodiments may be one or more tubes, pipes or other small containers. The selection of material to enclose the PCM is dependent upon the conditions which the PCM will be exposed to. The enclosure of one or more embodiments may be made from alumina ceramic (such as those of Fukahori et. al, Applied Energy, 170, 2016, p. 324-328) or various metals (such as those of Jacob et. al, Renewable and Sustainable Energy Reviews, 48, 2015, p. 79-87).

In some embodiments, the PCM may be encapsulated. In particular embodiments, the PCM may consist of small encapsulated particles (such as in US 2017/0283258 and US 2015/0190796).

PCM-Containing Reactors

The reactors of one or more embodiments of the present disclosure may include one or more catalysts and one or more PCMs. One of ordinary skill in the art will appreciate that the choice of catalyst is highly dependent on the reaction that is to be performed, and is not particularly limited. As discussed above, the selection of the PCM is primarily dependent upon the process conditions (i.e. temperature, pressure) of the reaction, and the catalytic inertness of the PCM.

The catalyst of one or more embodiments is not particularly limited. In some embodiments, it may be any dehydrogenation catalyst that is known in the art to effect the catalytic dehydrogenation of a hydrocarbon to generate an olefin. In one or more embodiments, the catalyst may be a dehydrogenation catalyst that is active for the conversion of propane to propene. In some embodiments, the catalyst may comprise a Group 4-6 metal oxide. In one or more embodiments, the catalyst may comprise a catalytically active material that is dispersed on a support. Such supports may be chosen to increase the surface area of the active material, and may be any known in the art. In particular embodiments, the support may be one or more of alumina, silica, and the like.

The reactor of one or more embodiments may further comprise an inert material. The choice of inert material is dependent upon the process at hand. For example, for a dehydrogenation reaction, such as the CATOFIN® process, the inert material may be chosen to provide a high heat capacity to limit the temperature change of the catalyst bed during the endothermic dehydrogenation reaction. In some embodiments, the inert material may be high density alumina. The inert material of some embodiments may be mixed with the catalyst in the catalyst bed. The physical form of the inert material is not particularly limited, but may be of a generally granulated or pelletized form. In a dehydrogenation process, the relative volumes of the inert material and the catalyst may depend on a number of factors including the type of hydrocarbon feed being used.

The reactor of one or more embodiments more may be a fixed-bed reactor or a fluidized-bed reactor. One of ordinary skill will appreciate that the type of reactor used is dependent upon the needs of the specific reaction to be performed. For instance, the CATOFIN® process generally utilizes a fixed bed reactor. The type of reactor used may influence the desired physical properties of the PCM. For example, the fluidized bed reactors of one or more embodiments may use an encapsulated PCM which has a small enough particle size and enough strength to pass through the fluidized bed. Such embodiments may allow for reduced catalyst/feed ratios.

The reactor of one or more embodiments may be prepared by physically combining the catalyst, the PCM, and, optionally, the inert material. The required amount of catalyst may be combined with a predetermined amount of PCM and inert material. One of ordinary skill in the art will appreciate that the relative amounts of these components are dependent upon the intended use of the reactor.

In one or more embodiments, the reactor of the present disclosure may include the PCM in an amount ranging from a lower limit of any of 1.0, 2.0, 4.0, 6.0, 8.0, and 10.0 wt. %, to an upper limit of any of 3.0, 5.0, 7.0, 9.0, and 15.0 wt. %, relative to the total weight of the reactor loading, where any lower limit may be used in combination with any mathematically-compatible upper limit. In one or more embodiments, the reactor of the present disclosure may include the PCM in an amount ranging from a lower limit of any of 1.0, 2.0, 4.0, 6.0, 8.0, and 10.0 vol. %, to an upper limit of any of 3.0, 5.0, 7.0, 9.0, and 15.0 vol. %, relative to the total volume of the reactor loading, where any lower limit may be used in combination with any mathematically-compatible upper limit.

In one or more embodiments, the reactor of the present disclosure may include the PCM in an amount ranging from a lower limit of any of 1.0, 2.0, 4.0, 6.0, 8.0, and 10.0 wt. %, to an upper limit of any of 15.0, 20.0, 25.0, 30.0, and 35.0 wt. %, relative to the total weight of the dehydrogenation catalyst, where any lower limit may be used in combination with any mathematically-compatible upper limit. In one or more embodiments, the reactor of the present disclosure may include the PCM in an amount ranging from a lower limit of any of 1.0, 2.0, 4.0, 6.0, 8.0, and 10.0 vol. %, to an upper limit of any of 15.0, 20.0, 25.0, 30.0, and 35.0 vol. %, relative to the total volume of the dehydrogenation catalyst where any lower limit may be used in combination with any mathematically-compatible upper limit.

The reactor of one or more embodiments, may place the PCM at a specific location relative to the catalyst in order to provide a desired heat transfer rate. In some embodiments, the PCM may be incorporated into a CATOFIN® reactor by storing it inside of sealed cylindrical tubes that are spaced apart in a grid pattern to evenly distribute the heat. The catalyst may be loaded around the cylinders to fill in the space.

The reactor of one or more embodiments may further comprise a heat-generating material (HGM). The HGM may be catalytically inert under the conditions of the process but may generate heat after being reduced and/or oxidized. Such a HGM may be any suitable material known in the art and for example, may be selected from copper, chromium, molybdenum, vanadium, cerium, yttrium, scandium, tungsten, manganese, iron, cobalt, nickel, silver, bismuth and combinations thereof. In one or more embodiments, the reactor may include the HGM in an amount ranging from a lower limit of 1.0, 3.0, 5.0, 7.0, or 9.0 wt. %, to an upper limit of 7.0, 9.0, 11.0, 13.0, 15.0, or 20.0 wt. %, where any upper limit may be used with any mathematically-compatible lower limit.

Processes

The process of one or more embodiments of the present disclosure may be directed to any endothermic catalytic reaction, and may include the use of any of the aforementioned catalyst beds that may be suitable. In particular embodiments, the process may be a cyclic process.

In some embodiments, the use of a PCM may increase the duration of a production cycle in reactors where a high portion of the heat of reaction is supplied by cooling the catalyst. For example, in a CATOFIN® process. Storing more energy in the catalyst bed, in the form of the latent heat of a PCM, may allow for a longer duration production cycle and a decreased regeneration cycle. In embodiments directed to, for example CATOFIN® processes, where the reactor dynamically alternates between dehydrogenation and regeneration cycles, the use of a PCM may reduce capital costs by decreasing the regeneration time of each reactor, meaning that fewer reactors are required to provide a given production capacity.

The CATOFIN® process of one or more embodiments may include the use of one or more PCM-containing reactors. Though the number of PCM-containing reactors is not particularly limited, in particular embodiments the process may involve the use of two reactors, four reactors, eight reactors, or ten reactors. The CATOFIN® process may be a continuous process wherein multiple PCM-containing reactors are operated in a cyclic manner, with a controlled sequence of dehydrogenation and reheat/regeneration.

During the dehydrogenation cycle of the CATOFIN® process of one or more embodiments, over time, heat is absorbed from the catalyst beds by the endothermic reaction as dehydrogenation proceeds, gradually reducing the temperature of the catalyst bed. This temperature reduction, coupled with coke deposited on the catalyst, decreases its ability to produce the desired products. However, when a phase transition temperature of the PCM is reached, the PCM may undergo an exothermic transition and provide heat to the catalyst bed, increasing the duration of the reaction cycle as compared to a conventional CATOFIN® process. However, to remove coke and to restore the necessary heat to the catalyst bed, periodic reheat of the catalyst with hot air is required.

In one or more embodiments, the use of a PCM may result in an increase in the duration of the dehydrogenation cycle, relative to the regeneration cycle. In some embodiments, the dehydrogenation cycle may have a duration that is 1.1 times or more, 1.2 times or more, 1.3 times or more, 1.4 times or more, or 1.5 times or more the duration of the regeneration cycle.

As such, the process of one or more embodiments may include one or more dehydrogenation reaction zones, with each zone including two or more reactors operating in parallel, where one reactor may be producing olefins and/or diolefins while the other reactor is being purged, and the catalyst regenerated and reheated to a desired reactor temperature before being brought back on line for olefin and/or diolefin production.

The dehydrogenation processes according to embodiments herein may include fixed-bed reactors which operate at low pressure and elevated temperature. The conditions may be selected to optimize the complex relationship among conversion, selectivity and energy consumption. The temperature and pressure may range from 400 to 750° C. and from 0.01 to 1 kg/cm$^2$ absolute, respectively. In particular embodiments, they may range from 575–650° C. and 0.1-0.5 kg/cm$^2$ absolute.

The processes of one or more embodiments may involve the dehydrogenation of one or more hydrocarbons. In some embodiments, one or more of the hydrocarbons may be selected from the C2-C5 aliphatic hydrocarbons. In particular embodiments, one or more of the hydrocarbons may be selected from propane, n-butane, and isobutane. In the reaction section, for instance, propane is converted to propylene, isobutane is converted to isobutene, and/or n-butane may be converted to n-butene and butadiene while passing through a PCM-containing catalyst bed. If both propane and butane processing is run simultaneously, separate dedicated C3 dehydrogenation reactors are used for the propane to propylene conversion and separate dedicated C4 dehydrogenation reactors are used for the butane to butene and/or isobutane to isobutene conversion. Reactor conditions (catalyst, catalyst loading, space velocity, hydrocarbon feed temperature, air/hydrocarbon ration, air temperature, etc.) may be optimized for the process to be performed in the reactor.

In one or more embodiments, side reactions occurring simultaneously with the main reaction cause the formation of some light hydrocarbon gases and heavy hydrocarbons, as well as the deposition of coke on the catalyst. The overall selectivity of propane to propylene is greater when dehydrogenating propane in a dedicated reaction zone, the overall selectivity of isobutane to isobutene is greater when dehydrogenating isobutane in a dedicated reaction zone, and the overall selectivity of n-butane to n-butenes/butadiene is greater when dehydrogenating n-butane/n-butenes in a dedicated reaction zone compared with selectivities that can be achieved when co-processing combinations of propane, isobutane and n-butane in the same reaction zone. In some embodiments, the overall selectivity of propane to propylene may be greater than 88 mole %, the overall selectivity of isobutane to isobutene may be greater than 90 mole %, and the overall selectivity of n-butane to n-butenes/butadiene may be greater than 60 mole %.

As described above, processes herein may include cyclic operations. Systems according to embodiments herein may include a control system configured for: operating one reactor in each of the reaction zones in a dehydrogenation cycle; operating one reactor in a regeneration cycle; and operating one reactor in a purge or evacuation/reduction cycle. The control system may be further configured for sequentially operating two or more valves disposed in a parallel flow arrangement for providing air, steam, and inerts, as required, from a common regeneration system to the reactors in the reheat/regeneration cycle and the reactor in the purge/evacuation/reduction cycle, and for providing propane, n-butane, and isobutane, as required, to the reactors in the dehydrogenation cycle. The control system, in other words, may be configured to operate the reactors in the dehydrogenation cycle in staggered cycles, such that the purge cycle, regeneration cycle, or evacuation/reduction cycle of the reactors do not overlap. Cycle timing instrumentation sequences the actuation of hydraulically operated valves to control the operation. The system may be suitably interlocked to ensure safe operation of the valves in sequence and prevent mixing of air and hydrocarbon gas.

After the dehydrogenation reaction cycle, while the reactor system is still under vacuum, the reactor may be thoroughly purged with steam, thereby stripping residual hydrocarbons from the catalyst and reactor into the recovery system. Reheat of the catalyst may be conducted at slightly above atmospheric pressure. Reheat air is supplied typically by a gas turbine or air compressor and heated to the required temperature in a direct-fired duct burner before passing through the reactors. The reheat air serves to restore both the temperature profile of the bed to its initial on-stream condition and catalyst activity, in addition to burning the coke off the catalyst. The reheat air leaving the reactors may be used to generate steam in a waste heat boiler.

When the reheat of a reactor is complete, the reactor is re-evacuated before the next on-stream dehydrogenation period. Prior to introducing hydrocarbon feed, hydrogen rich off-gas may be introduced to the reactor for a short time to remove absorbed oxygen from the catalyst bed. This reduction step decreases the loss of feed by combustion and restores the catalytic metal, such as chrome, on the catalyst to its active state. The reheat air stream leaving the reactors flows to the waste heat boiler which may be used to generate and superheat high pressure steam.

Embodiments herein may be used for any relative amounts of propylene, isobutene and butadiene production, and at any combination of capacities. Processes herein may be used for producing: propylene and isobutene, propylene and butadiene; isobutene and n-butadiene; propylene, isobutene and butadiene; and at any combination of product rates. In the case of butadiene production, n-butene may be extracted as a co-product. The plant may be designed for "once-thru" operation. In various embodiments, isobutane and n-butane may be processed together in the same dedicated dehydrogenation reactors; alternatively, isobutane and propane may be processed together in the same dedicated dehydrogenation reactors.

In one or more embodiments, any number of dehydrogenation reactors may be used according to the product capacities. The LTRU and distillation train may be customized based on product slate and capacities. Reactor conditions can be different for each dehydrogenation reactor during each cycle. Air flow and temperature may be changed during the reheat/regeneration step for each dehydrogenation reactor to maintain overall reactor heat balance. The distillation train may include a deethanizer, depropanizer and/or C3 Splitter for propylene production. The distillation train may also include a pre-fractionator for butadiene separation. A C2 splitter can be added to recover a high-purity ethylene product.

EXAMPLES

The following examples are merely illustrative and should not be interpreted as limiting the scope of the present disclosure.

The following process conditions were simulated for three examples:
Hydrocarbon Cycle:
Hydrocarbon Feed Temperature=578.8° C./851.9 K
Hydrocarbon WHSV=0.483 $h^{-1}$
Pressure=42 kPa (assumed constant in the reactor)
Steam Purge:
Ignored for this simulation
Air Regeneration Cycle:
Air Inlet Temperature=908.5 K
Air WHSV=3 1/h
Reduction:
Reduction Gas Inlet Temperature=783.9 K
Reduction Gas WHSV=0.3 1/h
Reduction Gas was set to be 60 vol % hydrogen

TABLE 1

Simulation Results

| | Example 1: Base Case | Example 2: Higher Cu on HGM | Example 3: Higher Cu and PCM |
|---|---|---|---|
| Reactor Loading (kg): | | | |
| Catalyst Mass | 6.945 | 6.945 | 6.945 |
| HGM Mass | 1.360 | 1.360 | 1.360 |
| Inerts Mass | 8.184 | 8.184 | 6.924 |
| PCM Mass | 0.000 | 0.000 | 1.188 |
| Cu on HGM (wt %) | 6 | 9 | 9 |
| Cycle Times (s): | | | |
| Hydrocarbon Cycle | 553 | 669.7 | 706.5 |
| Regeneration | 563 | 563 | 563 |
| Reducton | 84 | 84 | 84 |
| Max Bed Temp (K) | 913.3 | 925.9 | 925.4 |
| Cycle Avg. Conversion | 43.1% | 43.9% | 43.3% |
| Conversion at end of cycle | 40.7% | 40.7% | 40.7% |
| Cycle Avg. Selectivity | 90.7% | 89.4% | 90.5% |
| Cycle Avg. Yield | 39.1% | 39.2% | 39.1% |

The above examples demonstrate that the use of PCM enables a reactor to run for a longer period of time on the dehydrogenation cycle. This may ultimately result in higher catalyst utilization and having to build fewer reactors, which means lower capital costs for the construction of a CATOFIN unit.

Although the preceding description has been described herein with reference to particular means, materials and embodiments, it is not intended to be limited to the particulars disclosed herein; rather, it extends to all functionally equivalent structures, methods and uses, such as are within the scope of the appended claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed is:

1. A process for producing olefins, the process comprising:
   dehydrogenating a first alkane in a first reactor to produce a first effluent comprising at least one of a first n-olefin or a first diolefin;
   removing the first effluent from the first reactor; and
   regenerating the first reactor,
   wherein the first reactor comprises a fixed bed reaction zone containing first dehydrogenation catalyst particles disposed around sealed containers housing a first phase change material, wherein the sealed containers comprise sealed tubes that are spaced apart and arranged in a grid pattern within the fixed bed reaction zone; and
   wherein the dehydrogenation of the first alkane results in the temperature of the first phase change material to drop such that the first phase change material undergoes a phase transition.

2. The process of claim 1, wherein the phase transition of the first phase change material provides thermal energy to the first dehydrogenation catalyst that is sufficient to maintain the dehydrogenation of the first alkane.

3. The process of claim 1, wherein the dehydrogenation of the first alkane is performed for at least 1.2 times the duration of the regeneration of the first reactor.

4. The process of claim 1, wherein the first reactor contains the first phase change material in an amount of 5 to 30 wt. %, relative to the total weight of the dehydrogenation catalyst.

5. The process of claim 1, wherein the first reactor contains the first phase change material in an amount of 5 to 30 vol. %, relative to the total volume of the dehydrogenation catalyst.

6. The process of claim 1, wherein the first phase change material undergoes a phase transition at a temperature of 600° C. or more and 620° C. or less.

7. The process of claim 1, wherein the first alkane is one of the group consisting of propane, butane, and isobutane.

8. The process of claim 1, wherein the first phase change material comprises barium chloride and calcium chloride.

9. The process of claim 1, further comprising:
   dehydrogenating a second alkane in a second reactor to produce a second effluent comprising at least one of a second n-olefin or a second diolefin,
   removing the second effluent from the second reactor; and
   regenerating the second reactor,
   wherein the second reactor comprises a fixed bed reaction zone containing particles of a second dehydrogenation catalyst disposed around sealed containers housing a second phase change material, wherein the sealed containers are spaced apart within the second reactor fixed bed reaction zone and wherein the particles of second dehydrogenation catalyst fill a space between the sealed containers;
   wherein the second alkane is different from the first alkane; and
   wherein the dehydrogenation of the second alkane results in the temperature of the second phase change material to drop such that the second phase change material undergoes a phase transition.

10. The process of claim 9, wherein the second phase change material has a phase transition temperature different from that of the first phase change material.

11. The process of claim 1, wherein the sealed tubes comprise sealed cylindrical tubes.

12. A process for producing olefins, the process comprising:
    dehydrogenating a first alkane in a first reactor to produce a first effluent comprising at least one of a first n-olefin or a first diolefin;
    removing the first effluent from the first reactor; and
    regenerating the first reactor,
    wherein the first reactor comprises a first dehydrogenation catalyst particles and a first phase change material, wherein the first phase change material comprises barium chloride and calcium chloride; and
    wherein the dehydrogenation of the first alkane results in the temperature of the first phase change material to drop such that the first phase change material undergoes a phase transition.

13. The process of claim 12, wherein the first reactor contains the first phase change material in an amount of 5 to 30 wt. %, relative to the total weight of the dehydrogenation catalyst.

14. The process of claim 12, wherein the first reactor contains the first phase change material in an amount of 5 to 30 vol. %, relative to the total volume of the dehydrogenation catalyst.

15. The process of claim 12, wherein the first phase change material undergoes a phase transition at a temperature of 600° C. or more and 620° C. or less.

16. The process of claim 12, wherein the first alkane is one of the group consisting of propane, butane, and isobutane.

17. A process for producing olefins, the process comprising:
    dehydrogenating a first alkane in a first reactor to produce a first effluent comprising at least one of a first n-olefin or a first diolefin;
    removing the first effluent from the first reactor; and
    regenerating the first reactor,
    wherein the first reactor comprises a fixed bed reaction zone containing first dehydrogenation catalyst particles disposed around sealed containers housing a first phase change material, wherein the sealed containers are spaced apart and arranged in a grid pattern within the fixed bed reaction zone; and
    wherein the dehydrogenation of the first alkane results in the temperature of the first phase change material to drop such that the first phase change material undergoes a phase transition.

\* \* \* \* \*